United States Patent
McNamara et al.

(10) Patent No.: US 10,998,087 B2
(45) Date of Patent: May 4, 2021

(54) SYSTEMS AND METHODOLOGIES FOR DESIGINING SIMULANT COMPOUNDS

(71) Applicant: The Government of the United States of America, as represented by the Secretary of Homeland Security, Washington, DC (US)

(72) Inventors: Joseph McNamara, Egg Harbor City, NJ (US); Alexander DeMasi, Mays Landing, NJ (US); Michael Brogden, Galloway, NJ (US); Ronald Krauss, Galloway, NJ (US)

(73) Assignee: The Government of the United States of Amercia as represented by the Secretary of Homeland Security, Washington, DC (US)

( * ) Notice: Subject to any disclaimer, the term of this patent is extended or adjusted under 35 U.S.C. 154(b) by 33 days.

(21) Appl. No.: 15/246,729

(22) Filed: Aug. 25, 2016

(65) Prior Publication Data
US 2018/0060450 A1    Mar. 1, 2018

(51) Int. Cl.
*G16C 20/30* (2019.01)
*G16C 20/50* (2019.01)
*G16C 20/80* (2019.01)
*G06F 30/00* (2020.01)

(52) U.S. Cl.
CPC ............ *G16C 20/30* (2019.02); *G06F 30/00* (2020.01); *G16C 20/50* (2019.02); *G16C 20/80* (2019.02)

(58) Field of Classification Search
None
See application file for complete search history.

(56) References Cited

U.S. PATENT DOCUMENTS

| | | |
|---|---|---|
| 5,958,299 A | 9/1999 | Kury |
| 8,563,316 B2 | 10/2013 | Duffy |
| 2002/0069043 A1* | 6/2002 | Agrafiotis ............ B01J 19/0046 703/22 |

(Continued)

OTHER PUBLICATIONS

Stat-Ease, Inc. "Mixture Design Tutorial". in Design-Expert 9 User's Guide. Software documentation. May 2014.*

(Continued)

*Primary Examiner* — Soren Harward
(74) *Attorney, Agent, or Firm* — Lavanya Ratnam; Kelly G. Hyndman

(57) ABSTRACT

Systems and methods are provided for forming a simulant. In accordance with one embodiment, a method is provided for identifying and forming a simulant. The method identifies, using processing circuitry, a compound. The method further identifies, using the processing circuitry, a plurality of ingredients, wherein the simulant is a combination of the plurality of ingredients. The method further identifies for evaluation, using the processing circuitry, one or more metrics of the simulant. The method further determines, using the processing circuitry, proportions of each of the plurality of ingredients by optimizing a quadratic function based on the one or more metrics of the simulant. The method further outputs the proportions of each of the plurality of ingredients, and forms a mixture of the plurality of ingredients based on the proportions of each of the plurality of ingredients.

20 Claims, 4 Drawing Sheets

(56) References Cited

U.S. PATENT DOCUMENTS

| | | | |
|---|---|---|---|
| 2003/0033088 A1* | 2/2003 | Agrafiotis | B01J 19/0046 506/5 |
| 2004/0083083 A1* | 4/2004 | Doganaksoy | G06F 17/3053 703/6 |
| 2005/0089923 A9* | 4/2005 | Levinson | G06F 19/704 435/7.1 |
| 2005/0187748 A1* | 8/2005 | Chen | G06F 19/704 703/11 |
| 2007/0221087 A1* | 9/2007 | Adebimpe | A01K 15/02 102/355 |
| 2009/0194744 A1* | 8/2009 | Adebimpe | A01K 15/02 252/408.1 |
| 2013/0026420 A1* | 1/2013 | Duffy | F41H 11/136 252/408.1 |
| 2013/0041894 A1* | 2/2013 | DiZio | G06F 19/704 707/723 |
| 2014/0014829 A1* | 1/2014 | Barber | G01S 7/40 250/252.1 |

OTHER PUBLICATIONS

Ravindran, A., Ragsdell, K. M. & Reklaitis, G. V. Engineering Optimization. (John Wiley & Sons, Inc., 2006). Excerpt of p. 189.*

Kollat, J. B.; Reed, P. A Framework for Visually Interactive Decision-Making and Design Using Evolutionary Multi-Objective Optimization (VIDEO). Environmental Modelling & Software 2007, 22 (12), 1691-1704.*

Miettinen, K. Survey of Methods to Visualize Alternatives in Multiple Criteria Decision Making Problems. OR Spectrum 2014, 36 (1), 3-37.*

* cited by examiner

SYSTEMS AND METHODOLOGIES FOR DESIGINING SIMULANT COMPOUNDS

STATEMENT OF GOVERNMENT RIGHTS

This invention was made with government support under Contract No. HSHQDC-04-J-00001 awarded by the United States Department of Homeland Security. The government has certain rights in the invention.

BACKGROUND

Simulants are used in X-ray based Explosive Detection Systems (EDS) and X-ray or millimeter wave (MMW) based Advanced Imaging Technology (AIT) portals as a safe surrogate for training and testing purposes.

Explosive simulants are commonly used to field test various explosive detection systems and to train operators of such equipment. Explosive simulants are largely designed for X-ray imaging and explosive detection system (EDS) platforms, where an explosive's X-ray parameters are matched. The EDS is commonly used to identify explosives in luggage. However, the EDS platforms generally do not focus on aspects such as edge effects, compressibility, or flexibility of an explosive. While matching simulant and explosive morphology in a very general sense is possible, little has been done to determine the relevance of these types of material properties to EDS detection algorithms, or to measure and validate them. While these properties of simulants have not been critical in simulant development for EDS, they are much more relevant for simulants used for a different type of explosive detection system such as an Advanced Imaging Technology (AIT) portal.

AIT portals use detection algorithms that rely heavily on anomaly detection algorithms, and therefore it is imperative that simulants behave in a manner similar to that of the actual explosive. As such, when developing AIT portals, there is an ever-increasing need for simulants to match the morphological properties of explosives in order for simulants to become indistinguishable from live explosives.

AIT portals based on backscatter X-ray or millimeter wave (MMW) scanning technologies require validated simulants for testing and development. When used in MMW based AIT portals, simulants and explosives with similar dielectric properties produce similar grayscale responses. Regardless of the MMW dielectric response or the X-ray backscatter response, the AIT algorithm for threat detection is focused on anomaly identification, as opposed to material identification. The properties of the explosive or simulant that affect the image will be important; for MMW technology, the dielectric properties and the thickness determine the average reflectance, but the shape also affects the image. This shape, which includes the shape of the outer packaging as well as the thickness of the explosive or simulant material within the packaging, can be affected by the morphological properties.

Conventional methods for designing a new simulant that matches a particular explosive threat requires a trial and error process that may take many iterative steps, resulting in a loss of time and efficiency. Therefore, in view of the foregoing, there is a need for improved systems and methods for designing simulants.

SUMMARY

The present disclosure relates to a method for identifying and forming a simulant. The method may include identifying a compound using processing circuitry, and identifying a plurality of ingredients. The simulant can be a combination of the plurality of ingredients. In addition, the processing circuitry may identify one or more metrics for the simulant and determine proportions of each of the plurality of ingredients by optimizing a quadratic function based on the one or more metrics, and output the proportions of each of the plurality of ingredients.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
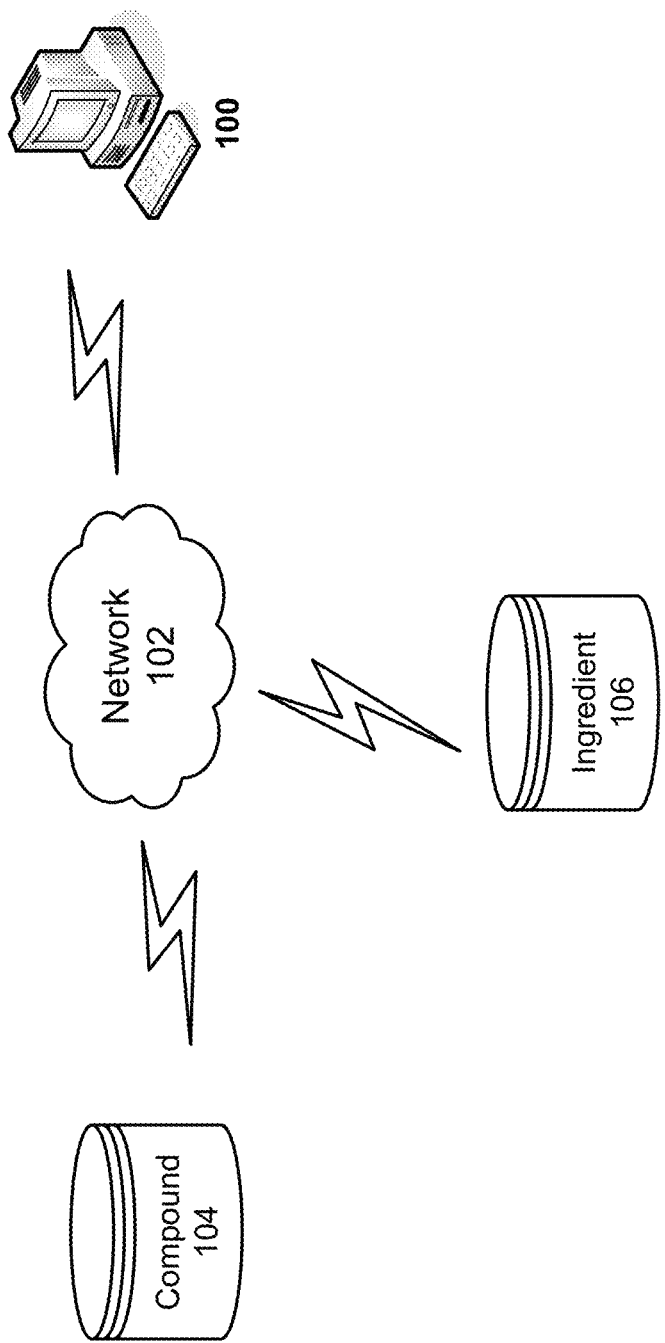
FIG. 1 is a schematic diagram of a system for identifying a simulant according to one example.

Referring now to the drawings, wherein like reference numerals designate identical or corresponding parts throughout several views, the following description relates to a system and associated methodology for identifying a simulant that matches characteristic properties of a compound (e.g., an explosive detector response, a flavor, a texture).

Simulants are needed for both training and testing explosive detection systems and advanced imaging technology portals. The simulants are used in place of live explosive threats in locations where live explosives cannot be used due to concerns of public safety. Although it is possible for a single ingredient to be a satisfactory simulant, simulants are usually physical mixtures of two or more non-explosive components (ingredients). Simulants are manufactured to produce the same detector response as live threats but as technology improves, more measurable properties may be needed for a given simulant to match a specific threat.

In one example, the system and associated methodology described herein model the characteristic properties of explosive threats for matching combinations of ingredients that generate a formula for making safe explosive simulants. Simulants are used as a safe surrogate for training and testing for threat detection in X-ray based explosive detection systems (EDS) and in X-ray based or millimeter wave (MMW) based advanced imaging technology (AIT) portals. Simulants are designed to produce the same detector response as explosive threats, but may also be designed to have the same properties as a threat as might be recognized by a human screener, such as color or texture.

Properties used as metrics for comparison between simulants and explosive threats are measurable or computable properties that may scale with weight percent, and can be added to a database of threats and simulant ingredients. When designing simulants, the objective is to match such metrics of the simulant to those of the actual explosive threat. Density and effective atomic number are two such properties that may be used for generating explosive simulants. Other physical attributes like color, particle size, and texture may also be used. The user may select a threat, simulant ingredients, and desired properties for optimization through, for example, a graphical user interface (GUI).

The methodology described herein provides an efficient and user-controlled way to design explosive simulants via matching tabulated physical properties of simulants to those of explosive threats. The claimed methodology can also be used with dielectric properties leading to simulant formulas that match both X-ray and MMW properties of targeted threat materials. The methodology may also be used to design simulants for other forms of contraband apart from explosive threats, such as explosive precursors, oxidizers, illegal drugs, or even innocuous materials, such as food products, by creating simulant mixtures that match (mimic) a set of targeted properties of threats and other forms of contraband.

The physical properties used as metrics to predict the properties that the new simulant would need to possess can be easily substituted. As described further below, the user may select one or more such metrics. The degree of matching (of a simulant to an explosive threat) can also be easily changed by selecting an optimization based on as many metrics as desired. The method described herein for improving the simulant design process optimizes the proportions of selected inert ingredients with calculated mixture percentages and returns a zero weight for selections that are not needed in the formula.

The methodology described herein allows a user to easily adjust from a very restrictive match of a given simulant's physical properties to a less restrictive match of a specific explosive threat if no viable solution is found. A plurality of metrics (properties) may be used. The plurality of metrics may include, but are not limited to, density, effective atomic number (Z-effective or $Z_{eff}$), mass attenuation coefficient (MAC), electron density, chemical compound ratio (e.g., Nitrogen-Oxygen to Carbon-Hydrogen ratio), dielectric constant, and millimeter wave reflectivity. The optimization may include one or more such metrics, or the reduction of the number of metrics to a limited number of properties to form a least restrictive match. For example, the optimization can be reduced to just one metric (e.g., density) as the least restrictive match. The methodology may also be extended to include additional metrics with no limitation on how many metrics are attempted to match a simulant to a specific explosive threat.

FIG. 1 is a schematic diagram of a system for identifying ingredients that comprise a simulant in order to provide a representation of a compound, which may be an explosive threat, according to one example. The system may include a computer 100, a network 102, a compound database 104, and an ingredient database 106. In one example, the compound database 104 and the ingredient database 106 may be cloud-based databases. The computer 100 may connect via communication circuitry through the network 102 with the compound database 104 and the ingredient database 106.

The compound database 104 includes a list of compounds, which may be threats. For each compound, the compound database 104 may store a plurality of metrics. For example, when the compound is an explosive, the plurality of metrics may include density, $Z_{eff}$, MAC, electron density, elemental ratios, and dielectric properties. The list of compounds may include explosive threats having various physical forms, including solids and powders (e.g., military explosives, aluminized explosives, trinitrotoluene (TNT), black powder, smokeless powder, or homemade explosives such as triacetone triperoxide (TATP)).

The ingredient database 106 may include a list of components that may be used to fabricate the simulant. For each component, the ingredient database 106 may store a plurality of metrics. In one example, computer 100 may receive a user input. The user input may include the identification of a compound, one or more ingredients, and a set of the plurality of metrics to be optimized. The system may output weight percentages of the one or more ingredients that mimic the plurality of metrics of the compound.

The computer 100 may include a CPU and a tangibly embodied computer-readable storage medium. The computer-readable storage medium may store instructions that, when executed by the CPU, perform steps in accordance with the disclosed embodiments. The databases 104 and 106 of the system may be implemented in the memory of the computer 100, or may be standalone databases as depicted in FIG. 1. Further, in some embodiments, the system may be implemented as an application that may be downloaded on a mobile device or a handheld computer.

The network 102 may include the Internet or any other network capable of communicating data between devices. Suitable networks can include or interface with any one or more of a local intranet, a PAN (Personal Area Network), a LAN (Local Area Network), a WAN (Wide Area Network), a MAN (Metropolitan Area Network), a VPN (Virtual Private Network), or a SAN (storage area network). Furthermore, communications may also include links to any of a variety of wireless networks, including WAP (Wireless Application Protocol), GPRS (General Packet Radio Service), GSM (Global system for Mobile Communication), CDMA (Code Division Multiple Access), TDMA (Time Division Multiple Access), cellular phone networks, GPS (Global Positioning System), CDPD (Cellular digit packet data), Bluetooth radio, or an IEEE 802.11 based radio frequency.

Figure 4:
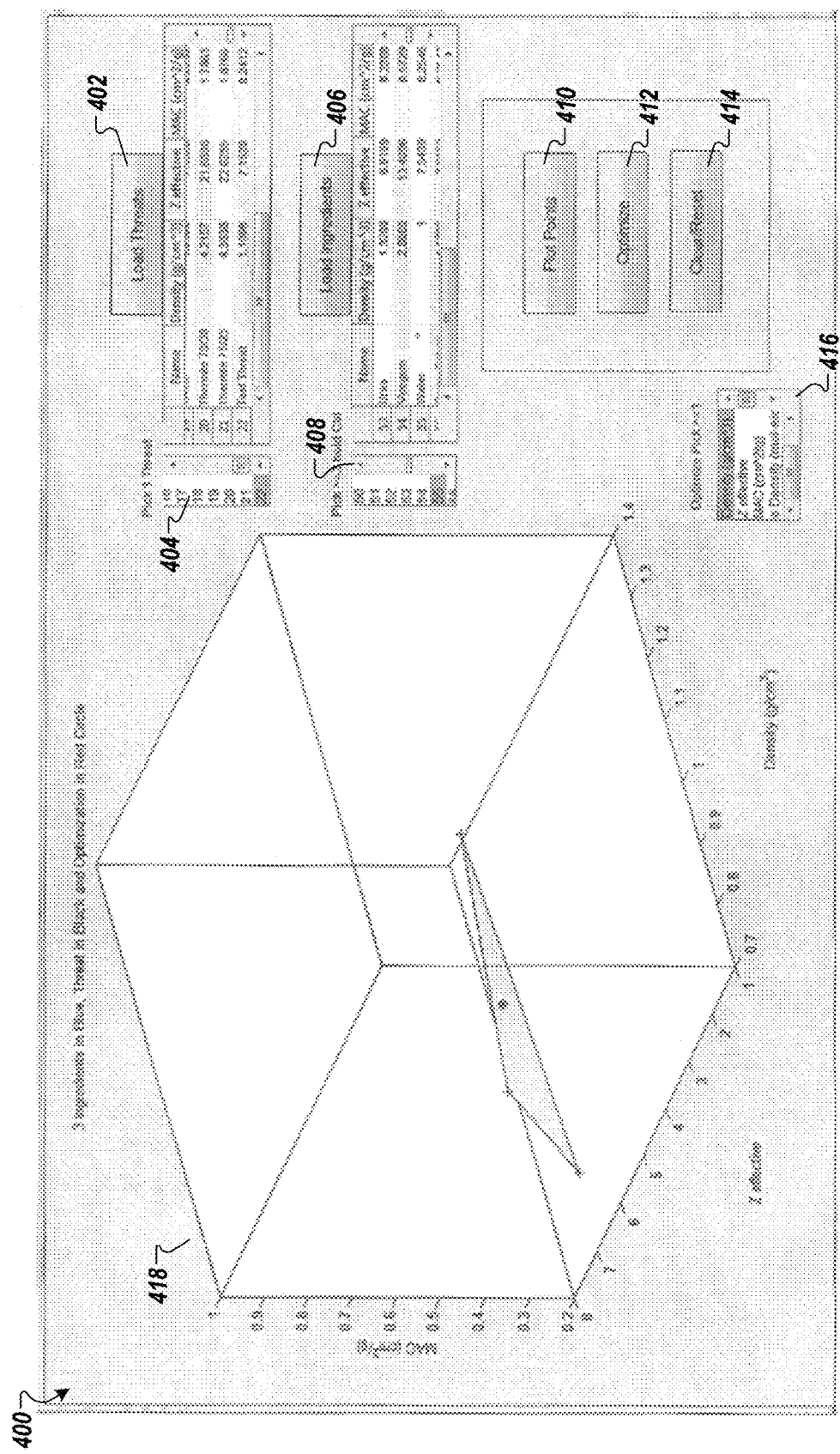
FIG. 4 is a schematic that shows a graphical user interface according to one example.

The CPU may minimize a quadratic function of three or more ingredients (of N-dimensions) with their weights subject to constraints. The dimension represents how many physical properties (metrics) are used in the optimization to match the formula to the compound (e.g., threat). The constraints for the weights are positivity (e.g., zero or positive weights) or normalization (e.g., all weights add to a predetermined number, for example, one). A GUI allows a user to perform various functions for formation of simulants, including selecting ingredients, a particular threat, and what properties to optimize for matching the formula to the selected threat. The results can be visualized with a 3-dimensional plot that can be rotated, an exemplary GUI of which is shown in FIG. 4. The GUI can also display the results of the optimization in the form of the rotatable 3-dimensional plot.

Figure 2:
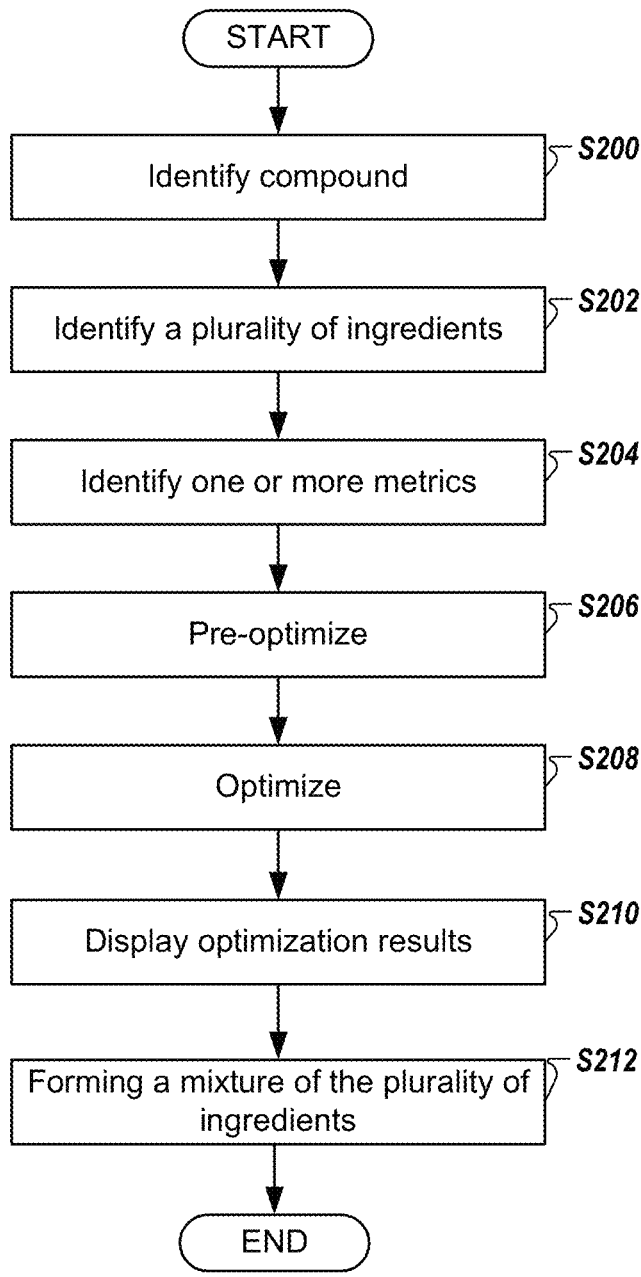
FIG. 2 is a flow chart illustrating a method for determining ingredients of the simulant according to one example.

FIG. 2 is a flow chart illustrating a method for formation of simulants that are designed to mimic threat compounds or materials, including the determination of the combination of ingredients that comprise the simulant, according to one example. The computational modeling tool described herein can calculate weight percent of ingredients that map to a specific point (target) representing the explosive threat.

At step S200, the CPU may identify a compound based on a user input. For example, the CPU may receive a user request indicating a compound. The compound may be a threat. The threat may be a combination of one or more existing materials (e.g., 59.6% RDX, 39.4% TNT, and 1% Paraffin wax).

At step S202, the CPU may identify a plurality of ingredients (components) to comprise the simulant design, in order to mimic the properties of the compound. In one example, the CPU identifies the plurality of ingredients based on the user input. Three or more ingredients may be identified, but the number of ingredients in the solution may be less (i.e., one or more ingredients may have zero weights).

At step S204, the CPU may identify one or more metrics. In one example, the CPU identifies the one or more metrics based on the user input. In other examples, the one or more metrics may be predetermined as a function of the compound type.

At step S206, the CPU may check to see whether the compound (e.g., threat) is a combination of existing materials before the optimization process of step S208 occurs. In response to the determination that the compound is a combination of existing materials, the CPU may determine the metrics values (e.g., density, $Z_{eff}$, MAC, etc.) of the compound based on the metrics values of each material. In addition, the CPU may use the elemental composition of the threats and ingredients as well as the NIST XCOM (National Institute of Standards and Technology Standard reference database). The CPU may connect via the network 102 to the NIST XCOM database to download and/or update metrics values associated with the compound and/or materials forming the compound. In performing this step, the list of potential ingredients may be further restricted as a way of pre-optimizing the simulant design.

At step S208, the CPU determines the weights, which may be percentages out of 100% or proportions of a number such as 1, of each of the plurality of ingredients identified at step S202 based on an optimization algorithm. The algorithm for optimization can be, for example, a quadratic programming technique that minimizes the total squared deviation of the weights from their mean; however, other optimization techniques may be utilized. In one example, the weight proportions or percentages (e.g. 0.47 or 5%, respectively) may be added together to form a predetermined number (e.g., 1 or 100% depending on whether weight proportions or percentages are used). In addition, the weights may be positive numbers (greater than or equal to zero). A solution exists if the N-dimensional target point (threat) lies within a convex set (convex hull) defined by the selected N-dimensional ingredient points. In one example, the CPU may minimize the quadratic function based on an interior point method as would be understood by one of ordinary skill in the art.

At step S210, the CPU may output the weights of the ingredients to the user. For example, the CPU may generate a three dimensional plot that displays the metrics of the simulant and the compound. In addition, the CPU may output the weights to an external device via the network 102.

At step S212, the simulant is formed based on the weights of the plurality of ingredients determined at step S208.

In one example, if the target point (threat or compound) does not lie within the convex set defined by the selected simulant ingredients, the user can then select different ingredients that do define a region around the threat and/or reduce the number of properties (a less restrictive match between the metrics of the simulant and those of the threat). Adding simulant ingredients may result in a better match, i.e. a simulant formula that is a better representation of the selected compound that is a threat. The more extensive the ingredient library file, the easier it is to find a match. However, in some cases the optimization may need to be made less restrictive (i.e., reduce the number of metrics that were used).

Figure 3:
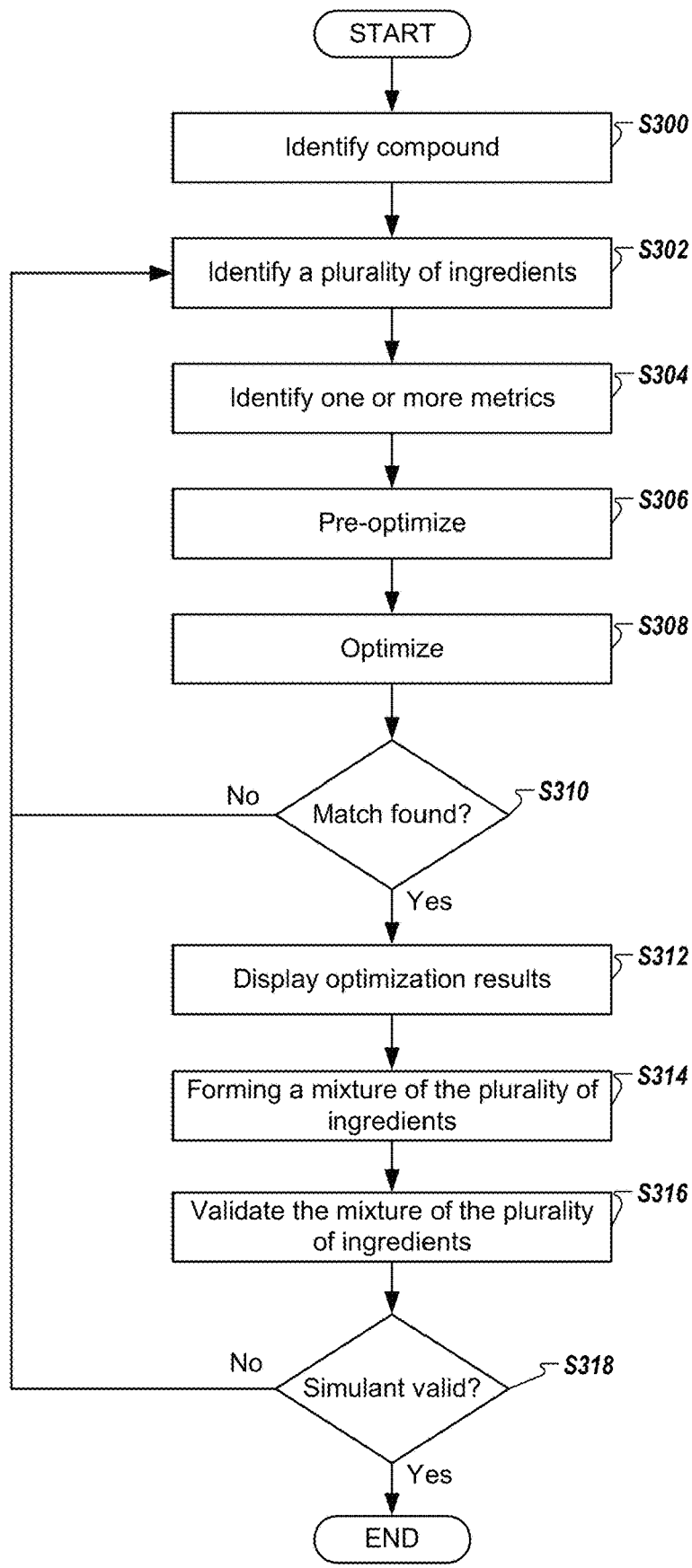
FIG. 3 is a flow chart illustrating a method for determining ingredients of the simulant according to one example.

FIG. 3 is a flow chart illustrating a method for formation of simulants to mimic compounds, including the determination of the combination of ingredients that comprise the simulant and the validation of the simulant, according to one example. At step S300, the CPU may identify a compound, which may be a threat that the simulant is meant to reproduce, based on a user input. For example, the CPU may receive a user request indicating a compound. At step S302, the CPU may identify a plurality of ingredients (components) of the simulant. In one example, the CPU identifies the plurality of ingredients based on the user input. At step S304, the CPU may identify one or more metrics. In one example, the CPU identifies the one or more metrics based on the user input. In other examples, the one or more metrics may be predetermined.

At step S306, in response to determining that the threat is a combination of existing materials, the CPU determines the metrics values of the compound based on the metrics values of each material. At step S308, the CPU determines the weights of each of the plurality of ingredients identified at step S302 as described previously with respect to FIG. 2.

At step S310, the CPU may check to see whether each metric of the simulant matches within a predetermined threshold with the corresponding metric of the compound. In response to determining, that the simulant matches each of the metrics, then the process goes to step S312. In response to determining, that the simulant does not match the compound, the flow of the method returns to step S302. At step S302, the user may be presented with the option to select more ingredients or alternative ingredients, in order to find a better match. In one example, the CPU may automatically identify one or more alternative ingredients that may be used. Furthermore, CPU may automatically identify the one or more alternative ingredients by comparing the similarity of one or more metrics of the simulant with metrics associated with the alternative ingredients, or with metrics of the compound.

At step S312, the CPU may output the weights of the ingredients to the user. For example, the CPU may generate a three dimensional plot that shows the metrics of the simulant and the compound. In addition, the CPU may output the weights to an external device via the network 102.

At step S314, the simulant is formed based on the weights of the ingredients determined at step S308. The simulant may be a packed powder mixture, a moldable plastic material, a solid material, gel or emulsion, or the like. In one example, the ingredients may be dry powder materials. In producing the simulant, a blend (according to the determined weights) of dry powder materials is placed into a custom-made tool and die set to form a mixture. Then, the mixture is compressed to fuse the materials together into a solid to reproduce the one or more metrics of a solid compound (e.g. solid explosive threat). In another example, the ingredients may be liquid materials. Then, a liquid mixture (according to the determined weights) of liquid materials may be formed to reproduce the one or more metrics of a liquid compound (e.g., liquid explosive threat).

At step S316, the simulant is validated by direct measurement of the one or more metrics, such as through the use of a variety of commercially available products for testing metrics such as density, $Z_{eff}$, etc.

At step S318, the CPU may compare the measured one or more metrics of the simulant with the one or more metrics of the compound to determine whether the metrics are within a predetermined threshold. If it is determined that the one or more metrics are within the predetermined threshold, then the process ends. However, if it is determined that the one or more metrics are not within the predetermined threshold, the process returns to step S302.

FIG. 4 is a schematic that shows a graphical user interface (GUI) 400 according to one example. The GUI 400 may be a part of a website, web portal, personal computer application, or mobile application configured to allow users to interact with the computer 100. The GUI 400 may include a "Load Threats" button 402, a "Pick Threat" control 404, a "Load Ingredients" 406, a "Pick Ingredients" 408, a "Plot Points" button 410, an "Optimize" button 412, a "Clear/Reset" button 414, a "Pick metrics" control 416, and a display pane 418.

Upon activation of the "Load Threats" button 402, the CPU retrieves a threat list from the threat database 104. For example, the CPU may retrieve the threat from the threat database 104 via the network 102. Upon activation of the "Pick Threat" control 404, the user may be presented with a drop-down menu, search box, or other selection control for identifying the compound (e.g., threat) to be matched.

Upon activation of the "Load Ingredients" button 406, the CPU retrieves an ingredients list from the ingredient database 106. Upon activation of the "Pick Ingredients" control 408, the user may be presented with a drop-down menu, search box, or other selection control for identifying the one or more ingredients.

Upon activation of the "Plot Points" button 410, the CPU may generate a three dimensional plot. In addition, the CPU may identify using a change in attribute (e.g., color) of the one or more ingredients, the compound, and the simulant (optimized material).

Upon activation of the "Optimize" button 412, the CPU calculates the weight of each ingredient as previously described in step S208.

Upon activation of the "Clear/Reset" button 414, the CPU may clear the selected one or more ingredients, the compound, and the calculated weights of each ingredients from the ingredient database 106.

Upon activation of the "Pick metrics" control 416, the user may be presented with the available metrics. The user may then select one or more metrics from the available metrics. The "display" pane 418 may show the 3D plot that depicts the metrics of the selected ingredients, the compound, and the simulant (optimized material). In one embodiment, the 3D plot has data points that are selectable and movable, such as by a user drag-and-drop operation. In this instance, a user can adjust the 3D plot to more closely conform to the compound metrics. The CPU may also identify alternative ingredients that would conform to the metrics represented by the modified 3D plot and may present to the user the identified alternative ingredients.

An additional "share" control (not shown), when selected, presents the user with options to share (e.g., email, print) results and/or parameters with an external device.

To illustrate the capabilities of methodologies described herein, exemplary results are presented.

In one example, three properties are investigated: density, $Z_{eff}$, and MAC that scaled perfectly with weight fraction. A test "threat" was created as a combination of three materials: 40% water, 40% corn syrup, and 20% ethanol. A test point was produced by multiplying the weights of each ingredient by the individual values of the three properties, and then summing them.

The optimization was run with water, corn syrup, and ethanol selected as the ingredients. The resulting formula was within ±0.005% of the original percentages for all three ingredients. Additional investigation was conducted to determine how these material properties scale with weight fraction. It was determined that some of these properties scale better than others. In response to such a determination, the optimized parameters may be modified.

As a test of the computational modeling tool, a simulant for 70% hydrogen peroxide (HP) is formulated based on matching theoretical density and $Z_{eff}$ values. The original simulant (SDL1B) consisted of 77.59% Karo light corn syrup, 20.46% distilled water, and 1.95% potassium meta-bisulfate, a combination of ingredient weights that was predicted using the methodology described herein. The density was measured with an Accupyc 1330 gas pycnometer from Micromeritics Instrument Corporation and the X-ray properties were measured on a Reveal CT80DR+EDS system from Leidos, Inc. The resulting data was then compared with data for 70% HP that already had been acquired on these systems. The resulting data is shown in Table 1 and Table 2. The density of the simulant was averaged over seven runs and the EDS measurements for the simulant were averaged over 15 scans. The SDL1B simulant was compared against a commercial-off-the-shelf (COTS) simulant and found to be better in only two of the five metrics as shown in Table 1 and Table 2. The formula was re-optimized using the methodology described herein and using the measured values (density and Z-effective) rather than theoretical values for the threat (70% HP). The resulting simulant (SDL2B) consisted of 75.35% Karo light corn syrup, 22.47% distilled water, and 2.18% potassium meta-bisulfate. All the differences of the five metrics for SDL2B compared with the threat were less than 1.35%. The second simulant (SDL2B) surpassed the COTS simulant in four of the five metrics measured.

TABLE 1

Experimental measurement data for 70% Hydrogen Peroxide and simulants

| Sample | Lot Number | Density Mean (g/cc) | Density SD (g/cc) | CT Z-Effective Mean | CT Z-Effective SD |
|---|---|---|---|---|---|
| 70% HP | 14k26 | 1.2820 | ±0.0010 | 7.645 | ±0.035 |
| HP Simulant SDL1B | 11May15 | 1.2847 | ±0.0005 | 7.601 | ±0.028 |
| Difference (%) | — | 0.21 | — | 0.58 | — |
| HP Simulant SDL2B | 1June15 | 1.2803 | ±0.0004 | 7.622 | ±0.020 |
| Difference (%) | — | 0.13 | — | 0.30 | — |
| HP Simulant COTS | 22Jan15 | 1.2851 | ±0.0004 | 7.617 | ±0.025 |
| Difference (%) | — | 0.24 | — | 0.37 | — |

TABLE 2

Experimental measurement data for 70% Hydrogen Peroxide and simulants

| | | High Energy | | Low Energy | | |
|---|---|---|---|---|---|---|
| Sample | Lot Number | CTN Average | CTN Mean SD | CTN Average | CTN Mean SD | CT Ratio |
| 70% HP | 14k26 | 12558.39 | ±193.26 | 12567.89 | ±150.52 | 1.0008 |
| HP Simulant SDL1B | 11 May 2015 | 12748.06 | ±185.91 | 12759.00 | ±155.78 | 1.0009 |
| Difference (%) | — | 1.51 | — | 1.52 | — | 0.01 |
| HP Simulant SDL2B | 1 Jun. 2015 | 12696.94 | ±192.06 | 12734.30 | ±135.49 | 1.0029 |
| Difference (%) | — | 1.10 | — | 1.32 | — | 0.21 |
| HP Simulant COTS | 22 Jan. 2015 | 12389.36 | ±207.53 | 12441.43 | ±171.59 | 1.0042 |
| Difference (%) | — | 1.35 | — | 1.01 | — | 0.34 |

Next, a hardware description of the computer 100 according to exemplary embodiments is described. As discussed above, the computer 100 includes a CPU which performs the processes described herein, and the process data and instructions may be stored in memory. These processes and instructions may also be stored on a storage medium disk such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computer 100 communicates, such as a server or computer.

Further, the claimed advancements may be provided as a utility application, background daemon, or component of an operating system, or combination thereof, executing in conjunction with the CPU and an operating system such as Microsoft Windows 7, UNIX, Solaris, LINUX, Apple MAC-OS and other systems known to those skilled in the art.

In order to achieve the computer 100, the hardware elements may be realized by various circuitry elements, known to those skilled in the art. For example, the CPU may be a Xenon or Core processor from Intel of America or an Opteron processor from AMD of America, or may be other processor types that would be recognized by one of ordinary skill in the art. Alternatively, the CPU may be implemented on an FPGA, ASIC, PLD or using discrete logic circuits, as one of ordinary skill in the art would recognize. Further, the CPU may also be implemented as multiple processors cooperatively working in parallel to perform the instructions of the inventive processes described above.

The computer 100 can also include a network controller, such as an Intel Ethernet PRO network interface card from Intel Corporation of America, for interfacing with network 102. As can be appreciated, the network 102 can be a public network, such as the Internet, or a private network such as LAN or WAN network, or any combination thereof and can also include PSTN or ISDN sub-networks. The network 102 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer 100 can further include a display controller, such as a NVIDIA GeForce GTX or Quadro graphics adaptor from NVIDIA Corporation of America, for interfacing with a display for implementing the GUI illustrated in FIG. 4. For example, the display may be a Hewlett Packard HPL2445w LCD monitor.

The exemplary circuit elements described in the context of the present disclosure may be replaced with other elements and structured differently than the examples provided herein.

The present disclosure is not limited to the specific circuit elements described herein. The present disclosure is also not limited to the specific sizing and classification of these elements. For example, the skilled artisan will appreciate that the circuitry described herein may be adapted based on changes on battery sizing and chemistry, or based on the requirements of the intended back-up load to be powered.

In one embodiment, a data processing system may be configured to perform the algorithms shown in FIGS. 2 and 3. The data processing system may include one or more processors and/or one or more heterogeneous processor systems.

The functions and features described herein may also be executed by various distributed components of a system. For example, one or more processors may execute these system functions, wherein the processors are distributed across multiple components communicating in a network. The distributed components may include one or more client and server machines, which may share processing in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input or received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

The hardware description above, exemplified by any one of the structure examples described above, constitutes or includes specialized corresponding structure that is programmed or configured to perform the algorithms shown in FIGS. 2 and 3.

A system which includes the features in the foregoing description provides numerous advantages to users. In particular, the system and associated methodology identifies a simulant. The methodology described herein could not be implemented by a human due to the sheer complexity of the process and calculations and includes a variety of novel features and elements that result in significantly more value than any construed abstract idea.

Numerous modifications and variations may be possible in light of the above teachings. Therefore, it is to be understood that, within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention or other claims. The disclosure, including any readily discernible variants of the teachings herein, defines, in part, the scope of the foregoing claim terminology such that no inventive subject matter is dedicated to the public.

The invention claimed is:

1. A method for identifying an explosive simulant, the method comprising:
   (a) displaying a listing of explosive threat compounds retrieved from a threat database based upon a user selection of a graphical user interface (GUI) control corresponding to the explosive threat compounds, wherein each explosive threat compound in the threat database is associated with one or more metrics having target values;
   (b) receiving a selection of an explosive threat compound from the displayed listing of explosive threat compounds using a selection control of the GUI;
   (c) displaying a listing of simulant ingredients retrieved from an ingredient database based upon the user selection of a GUI control corresponding to the simulant ingredients, wherein each simulant ingredient in the ingredient database is associated with one or more metrics having ingredient values;
   (d) receiving a selection of at least three ingredients from the displayed listing of simulant ingredients;
   (e) identifying for evaluation, using processing circuitry, one or more metrics based on the selected explosive threat compound, the one or more metrics being physical properties selected from the group consisting of density, electron density, effective atomic number ($Z_{eff}$), mass attenuation coefficient (MAC), chemical compound ratio, Nitrogen-Oxygen to Carbon-Hydrogen ratio, dielectric constant, and millimeter wave reflectivity;
   (f) determining, using the processing circuitry, proportions of each of the at least three ingredients by optimizing a quadratic function based on the one or more metrics of the simulant;
   (g) rendering, via the GUI, a three-dimensional (3D) plot that depicts the one or more metrics and a target point specified by the target values of the selected explosive threat compound, wherein the 3D plot has data points that are selectable and movable via the GUI to produce a new 3D plot representing modified metrics of the simulant,
   (h) when the target point specified by the target values of the selected explosive threat compound lies within a convex set defined by the quadratic function, outputting the determined proportions of each of the at least three ingredients, and
   (i) when the target point specified by the target values of the selected explosive threat compound does not lie within a convex set defined by the quadratic function, receiving user input to adjust the convex set by user selecting and moving the data points of the 3D plot to modify the metrics of the simulant to produce the new 3D plot, and identifying alternative ingredients and/or alternative proportions for one or more of the at least three ingredients that more closely conform to the target values of the explosive threat compound as represented by the user adjusted convex set, such that the alternative ingredients and/or alternative proportions serve as the at least three ingredients, and repeating step (f).

2. The method of claim 1, wherein the 3D plot has three axes corresponding to three metrics selected from the group consisting of density, electron density, effective atomic number ($Z_{eff}$), mass attenuation coefficient (MAC), chemical compound ratio, Nitrogen-Oxygen to Carbon-Hydrogen ratio, dielectric constant, and millimeter wave reflectivity.

3. The method of claim 1, wherein the explosive threat compound is an explosive, an explosive precursor, or a flammable material, and wherein the one or more metrics are density, effective atomic number, mass attenuation coefficient, electron density, chemical compound ratio, dielectric constant, or millimeter wave reflectivity.

4. The method of claim 1, further comprising:
   determining differences between the target values and the ingredient values of the selected at least three ingredients;
   determining whether the differences are greater than a predetermined threshold; and
   identifying one or more alternative ingredients when the differences are greater than the predetermined threshold.

5. The method of claim 4, further comprising determining whether metrics associated with the alternative ingredients fall within the predetermined threshold.

6. The method of claim 5, wherein the alternative ingredients are automatically identified and proposed based on similarity of metrics of the alternative ingredients to metrics values associated with the selected one or more ingredients identified for evaluation.

7. The method of claim 5, wherein the alternative ingredients are automatically identified and proposed based on similarity of metrics of the alternative ingredients to the target values.

8. The method of claim 1, further comprising (j) forming the simulant having at least one ingredient of the at least three ingredients based on the proportions of each of the at least three ingredients.

9. The method of claim 1, wherein the proportion of at least one of the at least three ingredients is optimized by the quadratic function to be zero.

10. The method of claim 1, wherein at least one of the threat database and the ingredient database are cloud based.

11. The method of claim 1, wherein optimizing the quadratic function comprises minimizing the quadratic function based on an interior point method.

12. The method of claim 1, wherein the 3D plot has three axes corresponding to the mass attenuation coefficient (MAC), effective atomic number ($Z_{eff}$), and density.

13. A system for identifying an explosive simulant, the system comprising:

one or more databases containing compounds and ingredients information, wherein each compound is associated with one or more metrics having target values, and each ingredient is associated with one or more metrics having ingredient values; and processing circuitry configured to:
(a) display a listing of explosive threat compounds retrieved from the one or more databases based upon a user selection of a graphical user interface (GUI) control corresponding to the explosive threat compounds;
(b) receive a selection of an explosive threat compound from the displayed listing of explosive threat compounds using a selection control of the GUI;
(c) display a listing of ingredients retrieved from the one or more databases based upon the user selection of a GUI control corresponding to the ingredients;
(d) receive a selection of at least three ingredients from the displayed listing of ingredients;
(e) identify for evaluation one or more metrics based on the selected explosive threat compound, the one or more metrics being physical properties selected from the group consisting of density, electron density, effective atomic number ($Z_{eff}$), mass attenuation coefficient (MAC), chemical compound ratio, Nitrogen-Oxygen to Carbon-Hydrogen ratio, dielectric constant, and millimeter wave reflectivity;
(f) determine proportions of each of the at least three ingredients by optimizing a quadratic function based on one or more metrics of the simulant;
(g) render, via the GUI, a three-dimensional (3D) plot that depicts the one or more metrics and a target point specified by the target values of the selected explosive threat compound, wherein the 3D plot has data points that are selectable and movable via the GUI to produce a new 3D plot representing modified metrics of the simulant,
(h) when the target point specified by the target values of the selected explosive threat compound lies within a convex set defined by the quadratic function, then output the determined proportions of each of the at least three ingredients, and
(i) when the target point specified by the target values of the selected explosive threat compound does not lie within a convex set defined by the quadratic function, receive user input to adjust the convex set by user selecting and moving the data points of the 3D plot to modify the metrics of the simulant to produce the new 3D plot, and identify alternative ingredients and/or alternative proportions for one or more of the at least three ingredients that more closely conform to the target values of the explosive threat compound as represented by the user adjusted convex set, such that the alternative ingredients and/or alternative proportions serve as the at least three ingredients, and repeat step (f).

14. The system of claim 13, wherein the 3D plot has three axes corresponding to three metrics selected from the group consisting of density, electron density, effective atomic number ($Z_{eff}$), mass attenuation coefficient (MAC), chemical compound ratio, Nitrogen-Oxygen to Carbon-Hydrogen ratio, dielectric constant, and millimeter wave reflectivity.

15. The system of claim 13, wherein the processing circuitry is further configured to:
determine differences between the target values and the ingredient values of the selected at least three ingredients;
determine whether the differences are greater than a predetermined threshold; and
identify one or more alternative ingredients when the differences are greater than the predetermined threshold.

16. The system of claim 15, wherein the processing circuitry is further configured to determine whether metrics associated with the alternative ingredients fall within the predetermined threshold.

17. The system of claim 16, wherein the processing circuitry is further configured to automatically identify and propose alternative ingredients based on similarity of metrics of the alternative ingredients to the one or more metrics of the explosive threat compound.

18. The system of claim 15, wherein the processing circuitry is further configured to display the alternative ingredients via the user interface.

19. The system of claim 13, further comprising (j) cause the simulant having the at least three ingredients based on the proportions of each of the ingredients to be formed.

20. The system of claim 13, wherein the 3D plot has three axes corresponding to the mass attenuation coefficient (MAC), effective atomic number ($Z_{eff}$), and density.

* * * * *